United States Patent [19]

Greenwood

[11] Patent Number: 4,615,792

[45] Date of Patent: Oct. 7, 1986

[54] HYDROGEN CIRCULATION FOR MOVING BED CATALYST TRANSFER SYSTEMS

[75] Inventor: Arthur R. Greenwood, Niles, Ill.

[73] Assignee: UOP Inc., Des Plaines, Ill.

[21] Appl. No.: 727,152

[22] Filed: Apr. 25, 1985

[51] Int. Cl.[4] ............................................ C10G 35/06
[52] U.S. Cl. .................................... 208/134; 208/165; 585/415; 585/654; 585/659
[58] Field of Search ................ 208/134, 165; 585/415, 585/654, 659

[56] References Cited

U.S. PATENT DOCUMENTS

| | | | |
|---|---|---|---|
| 2,303,717 | 12/1942 | Arveson | 208/165 |
| 3,238,122 | 3/1966 | Hagerbaumer | 208/165 |
| 3,647,680 | 3/1972 | Greenwood et al. | 208/165 |
| 3,725,249 | 12/1971 | Vesely et al. | 208/139 |
| 3,839,196 | 10/1974 | Plackmann et al. | 208/174 |
| 3,978,150 | 8/1976 | McWilliams, Jr. | 260/683.3 |

OTHER PUBLICATIONS

"Regenerate Reformers Continuously", by Bernard J. Cha, Roland Huin, Hugo Van Landeghem and Andre Vidal, from May 1973 issue of *Hydrocarbon Processing*.

*Primary Examiner*—Curtis R. Davis
*Attorney, Agent, or Firm*—Thomas K. McBride; John F. Spears, Jr.

[57] ABSTRACT

A system is disclosed for circulating an ancillary hydrogen-rich gas stream through a part of a moving bed hydrocarbon conversion process. The gas stream may be employed in lockhopper systems, catalyst transfer equipment and catalyst treating zones as for reducing the catalyst. The used ancillary gas is discharged into a partitioned vapor-liquid separation vessel. The partially condensed reaction zone effluent stream is discharged into a different chamber of the same vessel. The net off gas stream is withdrawn from the chamber receiving the used ancillary gas to prevent contamination of a recycle gas stream, which is drawn off the other chamber.

16 Claims, 1 Drawing Figure

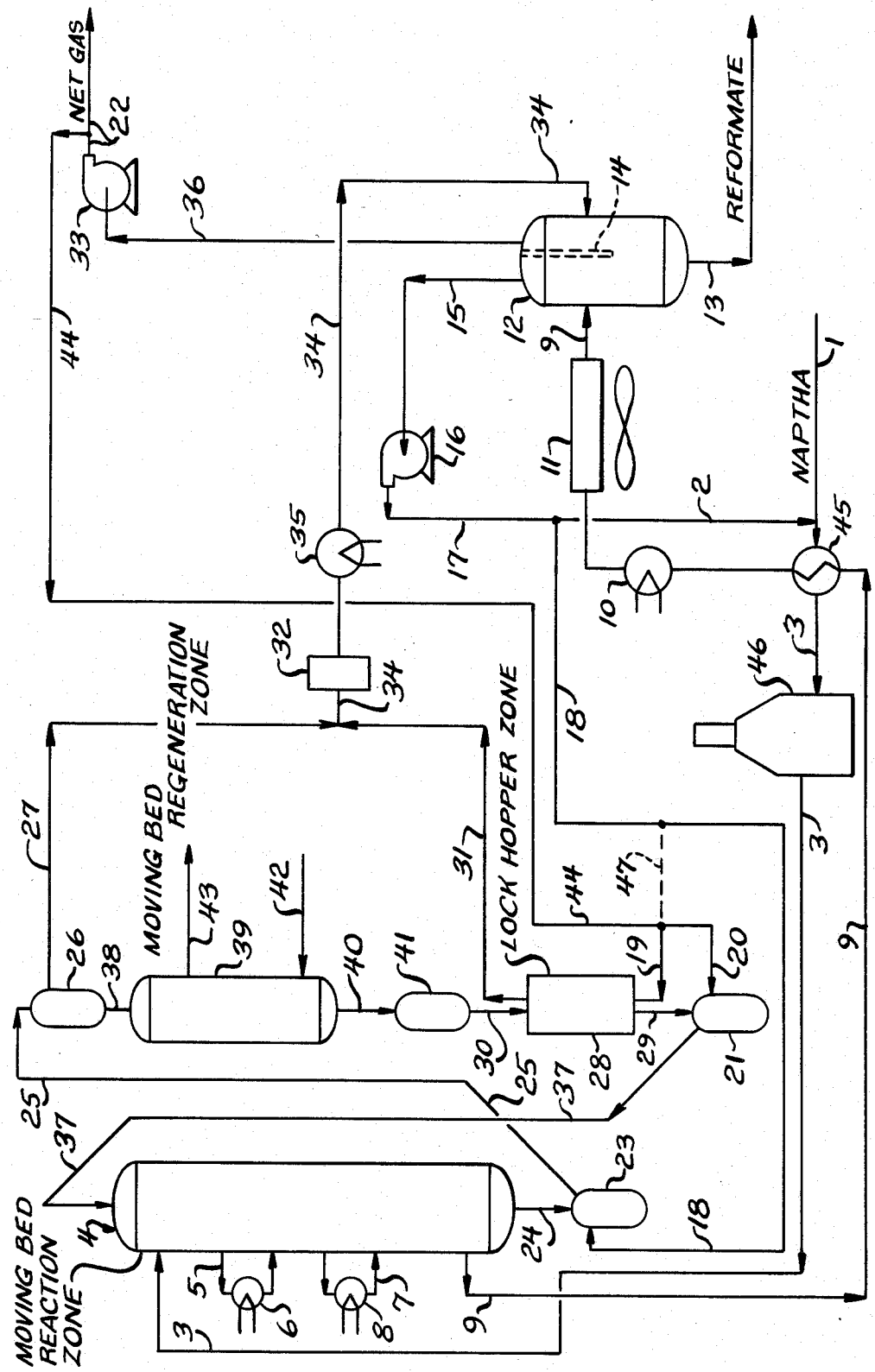

HYDROGEN CIRCULATION FOR MOVING BED CATALYST TRANSFER SYSTEMS

FIELD OF THE INVENTION

The invention relates to the operation of moving bed reaction systems employed in such hydrocarbon conversion processes as catalytic reforming, catalytic dehydrogenation, and dehydrocyclodimerization. The subject invention specifically relates to the apparatus employed in circulating catalyst particles through a moving bed reaction system. The invention therefore relates to the method and equipment employed to provide an ancillary gas stream, specifically hydrogen, used in elutriation, transportation, or purging of catalyst or employed in the reduction of metallic components of the catalyst. This includes the method by which hydrogen is provided for use in the lockhopper system used to transfer catalyst between the reaction zone and the regeneration zone of a continuous or moving bed catalytic reforming zone.

BACKGROUND INFORMATION

Those familiar with hydrocarbon conversion processes have long recognized that it would be advantageous to perform the processes in a continuous manner. This has prompted the development of moving bed catalytic processes. In these processes, the catalyst descends through a reaction zone in a compact, nonfluidized bed due to the action of gravity. That is, as catalyst is gradually removed from the bottom of the reaction zone, regenerated catalyst fed to the top of the reactor gradually moves downward to fill in the now available void spaces thereby providing a continuous bed of catalyst which is periodically changed. An early example of this type of reactor flow is provided in FIG. 3 of U.S. Pat. No. 2,303,717 issued to M. H. Arveson. This particular patent teaches the use of a moving bed reaction zone and a moving bed regeneration zone, the use of lockhoppers and stripping zones in catalyst treatment and transportation systems and the use of a conveying gas to lift catalyst from the bottom of the apparatus to the top of the apparatus. Another example of a moving bed hydrocarbon conversion process is presented in U.S. Pat. No. 3,238,122 issued to W. A. Hagerbaumer.

U.S. Pat. No. 3,725,249 issued to K. D. Vesely et al is pertinent for its teaching of a moving bed reforming operation with associated regeneration equipment. This reference is pertinent as the preferred embodiment of the subject invention is usage upon such a moving bed reforming operation. This reference is also pertinent for its overall teaching in regard to the use of lift engaging vessels to transport the catalyst, lockhoppers, and other catalyst handling techniques. U.S. Pat. No. 3,978,150 issued to F. G. McWilliams, Jr. is pertinent for its showing of a continuous or moving bed dehydrogenation process which employs similar catalyst transfer techniques including the utilization of a catalyst reducing zone as part of the regeneration procedure.

The above-cited references teach the use of nitrogen and methane to fluidize and transport catalyst upward from lift engaging vessels. The use of hydrogen to transport catalyst within such a moving bed process is also known as is shown by FIG. 1 of the article appearing at page 98 of the May, 1973 edition of *Hydrocarbon Processing*. U.S. Pat. No. 3,839,196 issued to the applicant indicates hydrogen used for such catalyst transport can be recycle gas recovered by separation from the effluent stream of the reaction zone.

It is believed that heretofore the gas stream employed in the lockhoppers and treating zones has been derived from gas supplied to the overall process from an outside source or from gas recovered at a point downstream from the reaction zone and then recycled or returned to the process. It is also believed that heretofore no attempt has been made to employ the products separator of the process as the receptacle of used auxiliary gas streams or to segregate various gases fed to the products separator.

SUMMARY OF THE INVENTION

The invention is an economical method of providing hydrogen-rich gas for use in catalyst transportation and in catalyst treating steps of a moving bed hydrocarbon conversion process. The invention employs a chambered vapor-liquid separation vessel to segregate impurity containing gas returned to this vessel from the reactor effluent gas which is also charged to this vessel. The impurity containing gas stream returned to the chambered separation vessel will normally be contaminated with water. The utilization of the chambered separation vessel allows the production of a substantially contaminant-free hydrogen recycle gas stream while simultaneously discharging at least the great majority of the contaminant from the process as part of the net gas stream.

A broad embodiment of the subject invention may be characterized as a moving bed hydrocarbon conversion process which comprises the steps of passing a particulate catalyst downward through a moving bed reaction zone wherein catalyst is contacted with hydrocarbons at hydrocarbon conversion conditions and producing spent catalyst and a reaction zone effluent stream comprising hydrocarbons and hydrogen; transporting spent catalyst into a regeneration zone wherein catalyst is contacted with an oxygen-containing gas at regeneration conditions and producing regenerated catalyst; passing the thus regenerated catalyst through a catalyst handling zone and then returning the catalyst to the reaction zone; separating the reaction zone effluent stream, by cooling and partial condensation, into a liquid hydrocarbon phase and a hydrogen-rich vapor phase which are separated in a vaporliquid separation vessel which has a gas receiving volume located in the upper portion of the vessel, which volume is partitioned into first and second collection chambers by a vertical partition, with the vapor phase portion of the reaction zone effluent entering the separation vessel via the first gas collection chamber; withdrawing the liquid hydrocarbon phase from the separation vessel and from the process; passing hydrogen-rich gas withdrawn from the first gas collection chamber of the separation vessel into the reaction zone as a recycle gas stream; passing additional hydrogen-rich gas withdrawn from the separation vessel through the catalyst handling zone wherein the gas contacts regenerated catalyst, and thus producing a catalyst handling zone gas stream; passing the catalyst handling zone gas stream into the second gas collection chamber of the separation vessel; and withdrawing the net off-gas stream from the process from the second gas collection chamber of the separation vessel. Preferably, the gas passed through catalyst handling zone is also withdrawn from the first gas collection chamber.

BRIEF DESCRIPTION OF THE DRAWING

The drawing is a schematic illustration of a moving bed catalytic reforming process in which hydrogen used in lock hopper zone 28 and the recycle gas of line 15 are withdrawn from a first compartment of the separation vessel 12 to avoid the presence in these gases of contaminants entering the vessel via line 34.

DETAILED DESCRIPTION

The hydrocarbon converion arts have for a long time recognized benefits which may be obtained by employing a moving bed reaction zone. Among these advantages are the ability to operate at a constant set of operating conditions and to produce a relatively uniform product during the course of operations. Other advantages include an ability to operate at a higher severity than would normally be commercially practical and the avoidance of periodic shutdown for catalyst replacement or regeneration. These advantages have prompted the development of moving bed reaction zones and catalyst handling systems. The improvement in these catalyst handling systems together with the availability of more attrition resistant catalyst has resulted in the use of moving bed reaction systems being commercially viable in a large number of hydrocarbon conversion processes including catalytic reforming, catalytic dehydrogenation, and dehydrocyclodimerization. The latter process is useful in the conversion of light aliphatic hydrocarbons such as propane or butylene into $C_6$-plus product hydrocarbons such as benzene, toluene, xylene and acyclic $C_6$ to $C_9$ hydrocarbons.

In the moving bed systems which are relevant to this invention the catalyst moves downward through a reaction zone by the action of gravity in the manner previously described. It is therefore necessary to peridically transport the catalyst upward to the top of the reaction zone or to the top of the regeneration zone. The exact transfer requirements and the number of times the catalyst must be transferred will be dependent upon the layout of the individual process. For instance, if the reaction zone is mounted directly above or below the regeneration zone, it is only necessary to transport the catalyst from the bottom of this combined circuit to the top of this circuit. In comparison, the reaction zone and the regeneration zone are more normally located side-by-side such that it is necessary to transport the catalyst from the bottom of the reaction zone to the top of the regeneration zone and simultaneously transport the catalyst from the bottom of the regeneration zone to the top of the reaction zone. This upward transportation of the catalyst could be obtained by various auger-type conveyers, buckets, or other mechanical contrivances. However, it is greatly preferred and it is the industry standard to transport the catalyst by means of a fluidizing gas which carries the catalyst as the gas passes upward through a conduit. In this mode of operation, the catalyst falls into a lift pot or lift engager and is then carried upward by a gas stream charged to the lift engager. This gas stream may be hydrogen, nitrogen, methane, or one of a number of other similar gases.

It is also customary to employ various lockhoppers within the catalyst transfer systems. For instance, lockhoppers provide a convenient safety measure to prevent the passage of combustible gas into the regeneration zone where it may become admixed with oxygen-containing gas. In a like manner, it is normally desired to employ some type of lockhopper or seal device between the regeneration zone and the reaction zone to prevent the passage of oxygen-containing gas into the reaction zone. Lockhoppers and other catalyst-handling zones or vessels are also employed within these processes for catalyst treating such as chlorination or metals reduction, or for pressurizing or depressurizing catalyst during the transportation of the catalyst through the overall system. Hydrogen and other gases are often used as the purge, pressurization or treating gas in these various lockhoppers and catalyst-treating zones.

It is an objective of the subject invention to provide a hydrogen-rich gas stream for use in treating, purging or transporting catalyst in a moving bed hydrocarbon conversion process. It is a further objective of the subject invention to provide a method for segregating contaminated hydrogen-rich gas streams which have been employed in catalyst-handling zones within the moving hydrocarbon conversion process and for discharging the contaminants from the process. In the subject invention, these objectives are obtained by providing a vertical baffle in the vapor-liquid separation zone (product separator) customarily employed in the product recovery section of the process. The entire effluent stream of the reaction zone is charged to one side of the baffled separation zone. The used and contaminant containing hydrogen-rich gases from the catalyst-handling zones are charged to the compartment of the separation vessel on the other side of this vertical baffle. The recycle gas stream is removed from the first side or compartment of the separation vessel. The net off-gas of the process is withdrawn from the second compartment which receives the contaminant containing catalyst-handling gas stream. The excess gas above that which is used as recycled gas passes under the vertical baffle and is also withdrawn together with the catalyst-handling gas stream. There is therefore a net flow of gas under the baffle which sweeps any of the gaseous contaminants upward and removes them as part of the net gas stream. Any condensed contaminants or particles which fall to the bottom of the separation vessel are removed with the hydrocarbon phase withdrawn from this vessel.

Referring now to the drawing, a naphtha stream enters the process through line 1 and is admixed with the recycle hydrogen stream from line 2. This admixture passes through the indirect heat exchange means 45 via line 3 and then enters a fired heater 46 wherein the temperature of the admixture is brought up the desired inlet temperature of the catalytic reforming zone. The heated admixture is then transported through line 3 to the inlet of the first stage of the multi-stage moving bed reaction zone 4. In the reaction zone shown in the drawing, the hydrogen-hydrocarbon mixture makes three separate passes through different catalyst beds retained within the reaction zone. As the reforming reaction is an endothermic one, the reactants are withdrawn through lines 5 and 7 for heating in the interstage heating devices 6 and 8. The reactor effluent stream, which is a totally vapor phase stream, is withdrawn through line 9 and passed through the feed-effluent heat exchanger 45 wherein it is normally partially condensed. Further heat is recovered in heat exchanger 10. The reactor effluent stream is then further cooled in the air cooled indirect heat exchange means 11. The effluent stream is then passed through a cooler not shown on the drawing. At this point, substantially all of the naphtha boiling range hydrocarbons are condensed except for the equilibrium amount of heavier hydrocarbons which remain in the hydrogen-rich vapor phase.

The gas-liquid admixture formed in this manner is charged into the vapor-liquid separation vessel 12 via line 9. The condensed liquid phase hydrocarbons are collected in the bottom portion of the separation vessel and withdrawn through line 13 as a reformate product stream. The uncondensed portion of the material entering the separation vessel through line 9 is divided into a major portion which rises upward and is removed through line 15 and a smaller portion which passes under the vertical imperforate baffle 14 into another compartment of the separation vessel. The portion of the vapor phase material delivered to the separation vessel via line 9 which is not removed through line 15 is withdrawn from the second compartment of the separation vessel through line 36 in admixture with a hereinafter described gas stream which is charged to the second compartment through line 34.

The baffle 14 segregates the gases entering the vapor-liquid separation vessel 12 into a product gas stream removed through line 36 and the recycle stream of line 15. The product gas is pressurized in the compressor 33 and then withdrawn from the process through line 22 as net gas after the diversion of any desired portion through line 44. The hydrogen-rich recycle gas stream removed in line 15 is pressurized in the recycle compressor 16 and then recycled to the process through lines 17 and 2.

The reforming reactions which occur in the reaction zone 4 result in the deposition of a hydrogen deficient hydrocarbonaceous material referred to in the art as coke upon the particulate catalyst employed in the reaction zone. This carbon-rich material has deleterious effects upon the activity of the catalyst caused by clogging available pore passageways within the catalyst and covering active catalytic sites. To counteract this deactivation used catalyst is slowly transferred downward through the reaction zone and eventually removed for regeneration through conduit 24 into the lift engaging vessel 23. The used catalyst is then fluidized upward through line 25 by means of a fluidizing or lift gas supplied to vessel 23 through line 18. The catalyst is thereby transferred to a disengagement vessel 26. Within this vessel, the catalyst is preferably separated from the lift gas and any fine materials caused by catalyst attrition in an elutriation device located within the vessel 26. The thus separated lift gas and fine catalyst particles are removed from vessel 26 through line 27. The used catalyst is then allowed to flow downward through conduit 38 into the moving bed regeneration zone labeled generally as 39. The downward rate of movement of catalyst through the regeneration zone and associated vessels, as well as the rate of downward movement of catalyst through the reaction zone, is governed by the rate of catalyst removal at the bottom of the respective zones.

The used catalyst is passed into the top of the regeneration zone through which it descends as a dense compact bed, such as an annular bed between porous screens, or as a cylindrical bed. In this zone the catalyst particles are preferably contacted with a circulating oxygen-containing gas stream passed into the reaction zone through line 42 and removed through line 43. In the preferred system, a large portion of the material existing through line 43 is returned to the regeneration zone through line 42, with some net gas being removed to compensate for an oxygen-containing gas stream which is admixed into the material flowing through line 42 at a rate set to maintain some preselective relatively low oxygen concentration in the gas stream. The temperature and oxygen concentration of this recycling gas stream are adjusted to maintain a regulated carbon burnoff and avoid overheating of catalyst. Other gas streams may be passed into or recirculated through the regeneration zone as desired in accordance with specific catalyst compositions or treating requirements for regeneration. For instance, it is normally desired to pass reforming catalyst through a drying zone. With the preferred platinum-containing reforming catalyst, it is normally desirable to subject the catalyst to a chlorination step within the regeneration zone subsequent to the carbon burnoff step. This is performed by contacting low carbon content catalyst produced by the coke burnoff operation with a chlorine containing gas stream. Further details on the operation of the regeneration zone and the passage of gas streams through this zone may be obtained by reference to U.S. Pat. Nos. 3,652,231; 3,981,824; and 4,094,817 which are hereby incorporated by reference into this application.

The thus treated catalyst is removed from the regeneration zone through the conduit 40 and passed into the intermediate lockhopper zone 41. This lockhopper zone may be supplied or utilized for the purposes of providing extra surge capacity within the reaction-regeneration catalyst circulation loop, for pressurization of the treated catalyst or for some other catalyst handling purpose. Catalyst is then withdrawn from lockhopper 41 via conduit 30 and passed into the lockhopper zone indicated generally as 28. It may be noted that catalyst flow control valves are often utilized at a number of locations within the catalyst circulation loop such as in conduits 38, 40, 30, and 24. These catalyst flow control valves also function to prevent the uncontrolled flow of various gases through the conduits. They therefore provide a safety measure by preventing the undesired admixture of hydrocarbonaceous and oxygen-contained gas streams and also permit the maintenance of substantially different pressures in various zones of the reaction-regeneration loop.

The lockhopper zone 28 may be employed to perform one or more individual catalyst-handling or treating functions. Preferably the catalyst is both pressurized and treated with a reducing gas stream within this zone. The function of contacting with the reducing gas stream is the reduction of the oxidation state of the metallic components of the reforming catalyst, which becomes oxidized during the carbon burnoff procedure performed in the regeneration zone. Preferably this metals reduction step is performed by contacting the low carbon catalyst with a reducing gas comprising hydrogen. The chemical reduction reaction results in the formation and release of water to the gases present in the zone 28. Another function of this catalyst handling zone is therefore the removal of this water from the catalyst. This is done by the reducing gas in a purging or high temperature drying step. The preferred hydrogen-rich gas employed in these steps enters lockhopper 28 through line 19 from a source described in more detail below. The hydrogen-rich gas preferably passes countercurrent to a descending bed of the catalyst or makes two or more passes through the descending catalyst in a countercurrent manner within the lockhopper zone 28. The fully conditioned and treated catalyst produced in this matter is then transferred through conduit 29 into the lift engaging vessel 21. The catalyst is then transported upwardly through conduit 37 to the top of the reaction zone 4 in admixture with a hydrogen-rich fluidizing gas charged to the lift engaging vessel through line 20. The catalyst is thereby circulated in a continuous loop passing repeatedly through the reaction zone and the regeneration zone. Catalyst may be supplied through a conduit not shown to compensate for any catalyst attrition.

The lift gas which is vented through line 27 will contain any catalyst fine particles or dust separated in the elutriation device provided within the disengaging hopper. The lockhopper zone effluent gas stream comprising the hydrogen-rich gas which has been used in catalyst treating steps performed within the lockhopper is removed through line 31 and is combined with the gas flowing through line 27. This combined gas stream flows through line 34 into a dust collection means 32. The combined gases then continue through line 34 and are cooled in the indirect heat exchange means 35 to a temperature essentially the same as the temperature of the effluent entering the separator 12 through line 9. The resultant effluent of the indirect heat exchanger 35 flows through line 34 and is passed into the separation vessel 12 on the opposite side of the baffle 14 from the incoming reactor effluent stream. The temperature of the material flowing through line 34 should normally be similar to that of the reaction zone effluent stream as it is passed into the receiving vessel 12 through line 9. A representative temperature for this gas stream is 100° F. By passing the gas stream of line 34 into the receiving vessel on the opposite side of the baffle, the water vapor and any dust particles still present within the gas stream despite filtration are withdrawn from the separation vessel in line 36. They therefore are not circulated back to the reaction zone or lockhopper zone via the recycle gas stream of line 15. Recycling an appreciable amount of water in the recycle stream is normally not desired as it would have detrimental effects upon the operation of the reaction and reduction zone.

In the embodiment of the invention shown in the drawing, a minor portion of the product gas which has been pressurized in the compressor 33 is diverted through line 44 for use as the fluidizing gas employed in the lift engager vessel 21 and as the gas employed in the lock hopper zone 28. It is recognized that the net gas stream will contain water vapor previously directed into the receiving vessel 12 through line 34. However, the water concentration in this gas stream will be lower than the water concentration in the gas stream carried by line 34 due to the dilution by relative dry gas spilling over at the bottom of the baffle 14. The utilization of gas diverted from line 22 is employed in this embodiment since it is already at the pressure required for injection of the gas into zones 21 and 28. It is therefore not necessary to install a separate compressing means for the purpose of providing gas to these zones. Further, it is not necessary as in some prior art applications to have an external or relatively high pressure gas stream supplied to the process. This gas stream is divided into two portions passed into the corresponding zones through lines 19 and 20 as required for the operation of those zones. This gas stream will normally be heated by means not shown prior to passing into the zones.

The relatively dry hydrogen-rich gas withdrawn from separation vessel 12 through line 15 is first pressurized in the recycle compressor and is then divided into the much larger portion carried by line 2 as the recycle gas stream and a much smaller portion carried by line 18 to the lift engaging zone 23. The lift engaging zone 23 would normally be operated at a lower pressure than the lockhopper zone 28 or the lift engager zone 21 such that the gas having a pressure equal to the discharge pressure of the recycle compressor may be employed for transferring the catalyst to disengaging vessel 26. This pressure would not normally be sufficient however for transferring catalyst from the lift engager 21 or for use within the lockhopper zone 28.

An alternative embodiment of the invention is shown on the drawing. This alternative embodiment may be employed when the discharge pressure of the recycle compressor 16 is sufficient that this hydrogen-rich gas stream can be employed in all of the catalyst handling or treating zones of the overall process. In this embodiment, a portion of the gas flowing through line 18 would be diverted through line 47, which is shown as a dashed line due to its optional nature, for passage into lines 19 and 20. In this alternative embodiment of the invention, line 44 would not be provided. If the pressures within the various components of the overall process permit, this alternative embodiment would become the preferred embodiments as all the hydrogen-rich gas employed in the catalyst handling steps would be of the relatively dry variety withdrawn to line 15. All of the water vapor charged to the receiving vessel 12 through line 34 would then be discharged from the process through line 22.

The use of the chambered vapor-liquid separation vessel 12 normally referred to as the product separation vessel has the advantage of simplifying and reducing the cost of the overall process. More specifically, the use of the chambered vessel allows one vessel to be employed for both the separation of the reaction zone effluent and for the separation of water vapor and any hydrocarbon condensate from the cooled gases which have been employed in the catalyst handling steps within the process. Therefore, the simple expedient of a mechanical barrier located within the receiving vessel eliminates the need for a second separation drum and any associated transfer lines, gauges, block valves, or liquid level control instrumentation, etc. which would be required for the auxiliary separator vessel.

It may be readily noted that the baffle 14 provided within the vessel can have several configurations. It is illustrated in its simplest form of a flat imperforate metal sheet extending across the upper half of the separation vessel. It is within the scope of the subject invention that the baffle 14 may be curved, angled, or in other ways shaped different than a flat partition. This baffle should definitely extend lower, at least 6 inches to one foot lower, than the lower of the two gas inlets to the vessel. It is preferred that the baffle does not extend down into the liquid hydrocarbon phase normally retained within the bottom of the separation vessel. However, it is foreseen that it may be desired to provide a gradually more foraminous partition which is essentially imperforate in its upper portion but has sufficient openings in a lower portion below the gas inlets to allow the gas to freely pass therethrough while still tending to restrict admixture of gases below the baffle. Such a system could be employed if there was concern about backmixing occurring within the vessel which would result in contamination of the relatively dry gas of line 15 with water vapor entering through line 34. It is highly preferred that a customary demisting pad be provided within both chambers of the separation vessel at a point above the gas inlet level.

The drawing is presented for the purposes of illustrating the subject invention and is not intended to restrict the use of the invention to apparatus of the manner depicted in the drawing. The subject process can therefore be employed with other processing arrangements such as different reaction zones or overall regeneration train configurations. For instance, the subject method could be employed in a process wherein separate individual reaction vessels arranged in a "side-by-side" configuration are employed as the reaction zone such as described in the previously cited *Hydrocarbon Processing* article. In this system, after passing through a first reaction stage the catalyst is transported via a lift engager and transfer lines to the top of a second reaction vessel through which it descends by the action of gravity. Three or more of such reactors can be employed in series. The hydrogen-rich gas supplied by the method of the subject invention can be employed in each of these required catalyst transfer steps including transfer of the catalyst from the last reaction stage to the top of a regeneration train. There may also be significant mechanical and structural variation in such items as the structure of the lift engaging vessel, the elutriation vessel, the control systems of the lockhopper and catalyst transportation systems, the internal configuration of the reaction zones and the regeneration zones and the valving and flow control systems employed in the process. Further details on these subjects may be obtained by reference to U.S. Pat. Nos. 3,825,116; 3,839;196; 3,839,197 and 3,856,662. The teaching of these four references is hereby incorporated by reference.

One embodiment of the invention may be characterized as a moving bed hydrocarbon conversion process which comprises the steps of passing particulate catalyst downward through a moving bed reaction zone wherein catalyst is contacted with reactants at hydrocarbon conversion conditions and producing spent catalyst and a reaction zone effluent stream comprising hydrocarbons and hydrogen; passing the spent catalyst through a first catalyst handling zone; transporting spent catalyst by means of a fluidization gas stream into a regeneration zone wherein catalyst is contacted with an oxygen-containing gas at regeneration conditions and producing regenerated catalyst; passing the regenerated catalyst through a second catalyst handling zone and then into the reaction zone; separating the reaction zone effluent stream, by cooling and partial condensation, into a liquid hydrocarbon phase and hydrogen-rich vapor phase which are separated in a vapor-liquid separation vessel which has a gas receiving volume located in the upper portion of the vessel, which volume is partitioned into at least a first and a second gas collection chamber by a vertical partition, with the vapor phase portion of the reaction zone effluent stream entering into the first gas collection chamber; withdrawing the liquid hydrocarbon phase from the separation vessel; withdrawing hydrogen-rich gas from the first gas collection chamber of said vessel, and passing said gas into the reaction zone as a recycle gas stream; withdrawing hydrogen-rich gas from the first gas collection chamber of said separation vessel, and passing said gas through the first catalyst handling zone wherein the gas contacts spent catalyst and employing said gas as the previously referred to fluidization stream, and removing the fluidization gas stream from the regeneration zone as a catalyst handling zone gas stream; passing the catalyst handling zone gas stream into the second gas collection chamber of said vessel; and withdrawing a net off-gas stream from the second gas collection chamber of said vessel, and removing the net off-gas stream from the process.

As previously mentioned, the subject method may be applied to a wide variety of processes including dehydrocyclodimerization or dehydrogenation of paraffinic hydrocarbons. The feed hydrocarbons for a dehydrogenation process employing a moving bed reactor would normally be one or more $C_2$ to $C_6$ straight chain or branched paraffinic hydrocarbons. Although it is possible to operate a dehydrogenation zone for the conversion of a mixture of two or more of such light hydrocarbons, it is preferred that the feed stream to the dehydrogenation zone is predominantly composed of hydrocarbons of a single carbon number range. Catalysts and operating conditions for dehydrogenation zones may be readily found in the available literature. A preferred dehydrogenation catalyst comprises spherical particles of alumina which supports active catalytic components. The active catalytic components preferably include platinum, a halogen such as chlorine and/or potassium and tin. Further information on a light paraffin dehydrogenation catalyst may be obtained by reference to U.S. Pat. No. 4,469,811. The effluent stream of the dehydrogenation reaction zone may be treated in the same manner as the effluent stream of the reforming zone shown in the drawing to provide a hydrogen-rich vapor phase and a liquid phase condensate stream which is sent to fractionation or other product recovery facilities.

When the subject process is employed for the dehydrocyclodimerization of acyclic hydrocarbons, the preferred feed stock is a $C_3$ to $C_5$ straight chain paraffinic hydrocarbon. The feed hydrocarbons to the dehydrocyclodimerization process may however contain significant amounts of olefins of the same carbon number. This process then produces an aromatic-rich product which contains a significant amount of branch chained $C_6$ to $C_9$ hydrocarbons depending on the feed composition. Again, the product of the dehydrocyclodimerization process may in general be recovered in a manner similar to that employed in the preferred reforming process, with the reaction zone effluent stream being subjected to a cooling and partial condensation to produce a vapor phase hydrogen-rich stream and a condensate stream comprised of the product and feed hydrocarbons. The liquid phase condensate would normally be transported to fractionation facilities for the separation of the remaining lighter feed hydrocarbons, which may be recycled to the reaction zone, from the heavier product hydrocarbons. Further details on this process are available from U.S. Pat. Nos. 3,756,922; 4,291,182; 4,157,356 and 4,354,049.

As also previously mentioned, the subject methods are preferably employed in conjunction with a process for the catalytic reforming of a naphtha boiling range hydrocarbon mixture. Such a naphtha mixture is typically recovered from a crude oil but could be derived from shale oil, tar sands, or from the liquefaction of coal or other hydrocarbonaceous materials. Reforming is performed to increase the octane number or aromaticity of a naphtha boiling range feedstock. Reforming is a vapor phase operation performed with a catalyst bed temperature in the range of about 750° F. to about 1050° F. It is normally not desired that the catalyst temperature exceeds about 1020° F. The other reforming conditions generally include a pressure of from about 20 psi to about 1000 psig, with pressures under about 150 psig being preferred, a liquid hourly space velocity of about 0.2 to 10.0 and a hydrogen to hydrocarbon mole ratio in the range of about 0.5:1.0 to about 10.0:1.0. The liquid hourly space velocity is the volumes of fresh charge stock contacted per hour divided by the volume of total catalyst particles. A preferred range for liquid hourly space velocities is from about 3.0 to about 8.0. The inlet temperature to the catalyst beds are normally maintained above about 950° F. Reforming catalyst typically contain one or more Group VIII noble metals (platinum, iridium, rhodium, and palladium) and a halogen such as chlorine and/or fluorine. These components of a catalyst are supported on a porous refractory carrier material such as alumina. The reforming catalyst may also contain one or more metallic catalytic components such as rhenium, germanium, or tin with the presence of tin presently being preferred in the catalyst. Further details on catalyst suitable for catalytic reforming may be obtained by reference to U.S. Pat. Nos. 3,740,328; 3,745,112; 3,948,804; and 4,367,137. The preferred physical form of the catalyst for use in a moving bed reaction and regeneration train is in the form of hard spherical particles having a diameter of from about 1/64 to about 5/32 of an inch.

The vapor phase effluent stream of the reforming reaction zone is preferably handled in a manner similar to that shown in the drawing. That is, the vapor phase effluent stream is subjected to heat exchange to recover useful heat and is then further cooled to effect a partial condensation and the production of the mixed phase effluent stream which is charged into the vapor-liquid separation vessel. The separation vessel would normally be operated at a pressure slightly reduced from the pressure maintained within the reaction zone. The separation vessel may therefore be operated at a pressure of from about 10 to about 950 psig with pressures under about 145 psig being preferred. The separation vessel would normally be operated at a temperature of from about 85 to about 155° F. The liquid phase condensate removed from the bottom of the separation vessel is preferably subjected to a recontacting step in which it is pressurized and combined with the compressed vapor phase material removed from the top of the separation vessel for the purposes of increasing the purity of the recovered hydrogen and increasing the liquid hydrocarbon yield. After this recontacting step, the liquid and vapor phases are once again separated, with the liquid phase at this time being transported to fractionation facilities. Typically, the primary stage of the fractionation facilities consists of a debutanizer column. Suitable product recovery techniques are described in the prior art including U.S. Pat. Nos. 3,882,014 and 4,364,820.

I claim as my invention:

1. A moving bed hydrocarbon conversion process which comprises the steps of:
    (a) passing particulate catalyst downward through a moving bed reaction zone wherein catalyst is contacted with hydrocarbons at hydrocarbon conversion conditions and producing spent catalyst and a reaction zone effluent stream comprising hydrocarbons and hydrogen;
    (b) transporting spent catalyst into a regeneration zone wherein spent catalyst is contacted with an oxygen-containing gas at regeneration conditions and producing regenerated catalyst;
    (c) passing the regenerated catalyst through a catalyst handling zone and then into the reaction zone;
    (d) separating the reaction zone effluent stream, by cooling and partial condensation, into a liquid hydrocarbon phase and hydrogen-rich vapor phase which are separated in a vapor-liquid separation vessel which has a gas receiving volume located in the upper portion of the vessel, which volume is partitioned into at least first and second gas collection chambers by a vertical partition, with the vapor phase portion of the reaction zone effluent stream entering the separation vessel via the first gas collection chamber;
    (e) withdrawing the liquid hydrocarbon phase from the separation vessel as a product stream;
    (f) passing hydrogen-rich gas withdrawn from the first gas collection chamber of said separation vessel into the reaction zone as a recycle gas stream;
    (g) passing hydrogen-rich gas withdrawn from said separation vessel through the catalyst handling zone wherein the gas contacts regenerated catalyst, and producing a catalyst handing zone gas stream.
    (h) passing the catalyst handling zone gas stream into the second gas collection chamber of said vessel; and,
    (i) withdrawing a net off-gas stream from the second gas collection chamber of said vessel, and removing the net off-gas stream from the process.

2. The process of claim 1 further characterized in that the catalyst handling zone comprises a reduction zone in which regenerated catalyst is contacted with a hydrogen-containing gas and metallic components of the catalyst are converted to a lower oxidation state.

3. The process of claim 2 further characterized in that the hydrogen-rich gas passed through the catalyst handling zone is withdrawn from the first gas collection chamber of the separation vessel.

4. The process of claim 3 further characterized in that the hydrocarbon conversion process comprises the catalytic reforming of naphtha boiling range hydrocarbons.

5. The process of claim 1 further characterized in that the hydrogen-rich gas passed through the catalyst handling zone is withdrawn from the second gas collection chamber of the separation vessel.

6. The process of claim 5 further characterized in that the hydrocarbon conversion process comprises the catalytic reforming of naphtha boiling range hydrocarbons.

7. A moving bed hydrocarbon conversion process which comprises the steps of:
    (a) passing particulate catalyst downward through a moving bed reaction zone wherein catalyst is contacted with reactants at hydrocarbon conversion conditions and producing spent catalyst and a reaction zone effluent stream comprising hydrocarbons and hydrogen;
    (b) passing the spent catalyst through a first catalyst handling zone;
    (c) transporting spent catalyst by means of a fluidization gas stream into a regeneration zone wherein catalyst is contacted with an oxygen-containing gas at regeneration conditions and producing regenerated catalyst;
    (d) passing the regenerated catalyst through a second catalyst handling zone and then into the reaction zone;
    (e) separating the reaction zone effluent stream, by cooling and partial condensation, into a liquid hydrocarbon phase and hydrogen-rich vapor phase which are separated in a vapor-liquid separation vessel which has a gas receiving volume located in the upper portion of the vessel, which volume is partitioned into at least first and second gas collection chambers by a vertical partition, with the vapor phase portion of the reaction zone effluent stream entering into the first gas collection chamber;

(f) withdrawing the liquid hydrocarbon phase from the separation vessel;

(g) passing hydrogen-rich gas withdrawn from the first gas collection chamber of said vessel into the reaction as a recycle gas stream;

(h) passing hydrogen-rich gas withdrawn from the first gas collection chamber of said separation vessel through the first catalyst handling zone wherein the gas contacts spent catalyst, employing said gas as the previously referred to fluidization gas stream, and removing the fluidization gas stream from the regeneration zone as a catalyst handling zone gas stream;

(i) passing the catalyst handling zone gas stream into the second gas collection chamber of said vessel; and, (j) withdrawing a net off-gas stream from the second gas collection chamber of said vessel, and removing the net off-gas stream from the process.

8. The process of claim 7 further characterized in that the first catalyst handling zone comprises a catalyst lift engaging vessel used to transport catalyst to the regeneration zone.

9. The process of claim 7 further characterized in that hydrogen-rich gas withdrawn from the first gas collection chamber of the separation vessel is passed through the second catalyst handling zone.

10. The process of claim 9 further characterized in that metallic components of the catalyst are reduced to a lower oxidation state within the second catalyst handling zone.

11. The process of claim 10 further characterized in that a hydrogen-rich return gas stream which comprises water vapor is withdrawn from the second catalyst handling zone and passed into the second gas collection chamber of the separation vessel.

12. The process of claim 11 further characterized in that a hydrocarbon conversion process is the catalytic reforming of naphtha boiling range hydrocarbons.

13. The process of claim 7 further characterized in that hydrogen-rich gas withdrawn from the second gas collection chamber of the separation vessel is passed through the second catalyst handling zone in a manner which effects the reduction to a lower oxidation state of the metallic components of the catalyst and the production of a hydrogen-rich return gas stream which comprises water vapor, and in the return gas stream is passed into the second gas collection chamber of the separation vessel.

14. The process of claim 13 further characterized in that the hydrocarbon conversion process is the catalytic reforming of naphtha boiling range hydrocarbons.

15. The process of claim 7 further characterized in that the hydrocarbon conversion process is the dehydrogenation of a $C_2$ to $C_6$ paraffinic hydrocarbon.

16. The process of claim 7 further characterized in that the hydrocarbon conversion process is the dehydrocyclodimerization of a $C_3$ to $C_5$ acyclic hydrocarbons.

* * * * *